(12) United States Patent
Lowry

(10) Patent No.: US 10,675,084 B2
(45) Date of Patent: *Jun. 9, 2020

(54) CAUTERY PROTECTIVE ACCESSORY SLEEVE WITH STABILIZATION SYSTEM

(71) Applicant: Suzanne Lee Lowry, Atlanta, GA (US)

(72) Inventor: Suzanne Lee Lowry, Atlanta, GA (US)

( * ) Notice: Subject to any disclaimer, the term of this patent is extended or adjusted under 35 U.S.C. 154(b) by 696 days.

This patent is subject to a terminal disclaimer.

(21) Appl. No.: 15/332,957

(22) Filed: Oct. 24, 2016

(65) Prior Publication Data

US 2017/0100185 A1  Apr. 13, 2017

Related U.S. Application Data

(63) Continuation-in-part of application No. 13/905,069, filed on May 29, 2013, now Pat. No. 9,474,572.

(Continued)

(51) Int. Cl.
*A61B 18/14* (2006.01)
*A61B 18/00* (2006.01)
*A61B 90/00* (2016.01)

(52) U.S. Cl.
CPC ...... *A61B 18/1477* (2013.01); *A61B 18/1402* (2013.01); *A61B 2018/00595* (2013.01);
(Continued)

(58) Field of Classification Search
CPC . A61B 18/14; A61B 18/1402; A61B 18/1477; A61B 2018/00595;
(Continued)

(56) References Cited

U.S. PATENT DOCUMENTS

| 5,318,565 | A | | 6/1994 | Kuriloff et al. |
| 5,527,313 | A | * | 6/1996 | Scott ............... A61B 17/2909 606/41 |

(Continued)

FOREIGN PATENT DOCUMENTS

CN  203252722 U  10/2013

OTHER PUBLICATIONS

International Search Report & Written Opinion dated Jan. 12, 2018 from PCT Application No. PCT/US17/58090.

*Primary Examiner* — Michael F Peffley
*Assistant Examiner* — Khadijeh A Vahdat
(74) *Attorney, Agent, or Firm* — Innovation Capital Law Group, LLP; Vic Lin

(57) ABSTRACT

A cautery pen tip accessory cover comprises a cylindrical member that can receive a cautery pen in a first end and the tip of the cautery pen can extend from a second opposite end when the cover is in a retracted configuration. The cylindrical member has an opened lateral exposure that allows the feel of the cautery pen therethrough. A cover exposure opening in the cylindrical member to provide access to a trigger of the cautery pen when the cautery pen tip cover is in the retracted configuration. A resilient member urges the cautery pen tip cover to the non-retracted configuration where access to the cautery pen trigger is prevented. The cylindrical member is easily retracted by a finger ring configured permanently into the cylindrical member, allowing easy retraction of the cover by the operator squeezing the cover to a resistance bar stabilization system accessory configured over the cautery pen.

20 Claims, 11 Drawing Sheets

Related U.S. Application Data

(60) Provisional application No. 61/689,108, filed on May 30, 2012.

(52) U.S. Cl.
CPC ............... *A61B 2018/1475* (2013.01); *A61B 2090/0481* (2016.02); *A61B 2218/007* (2013.01)

(58) Field of Classification Search
CPC .... A61B 2018/1475; A61B 2090/0481; A61B 2218/007; C07D 231/06; C07D 231/54; C11D 3/42
USPC ...................................... 606/41–50
See application file for complete search history.

(56) References Cited

U.S. PATENT DOCUMENTS

| | | | |
|---|---|---|---|
| 7,749,221 B2* | 7/2010 | Rontal | A61B 18/1402 606/41 |
| 2007/0179340 A1* | 8/2007 | Jorgensen | A61B 1/04 600/139 |
| 2007/0276189 A1 | 11/2007 | Abel et al. | |
| 2012/0259357 A1 | 10/2012 | Elliott | |
| 2012/0316554 A1 | 12/2012 | Baron et al. | |
| 2013/0325005 A1 | 12/2013 | Lowry | |
| 2015/0374363 A1 | 12/2015 | Laurent et al. | |

\* cited by examiner

CAUTERY PROTECTIVE ACCESSORY SLEEVE WITH STABILIZATION SYSTEM

CROSS-REFERENCE TO RELATED APPLICATIONS

This application is a continuation-in-part of U.S. patent application Ser. No. 13/905,069, filed May 29, 2013, now U.S. Pat. No. 9,474,572, which claims the benefit of priority of U.S. Provisional patent application No. 61/689,108, filed May 30, 2020, the contents of which are herein incorporated by reference.

BACKGROUND OF THE INVENTION

1. Field of the Invention

One or more embodiments of the invention relates generally to electrocautery accessories. More particularly, the invention relates to a compression spring automated retractable protective electrocautery pen tip cover.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Many cautery devices alert the physician and staff of their actuation through a high-pitched sound. However, this sound is often not heard secondary to all of the many devices in the operating room which make high pitched sounds.

Currently, the only option to assure that the pen is not accidentally actuated by either the surgeon, the staff or even the patient, is to place the pen in a large, clumsy plastic box, often referred to as a holster, that is clipped to the operating field. This box is so large that nothing assures that the pen stays in place, other than staff vigilance.

If the pen is dislodged, it can accidently be actuated and could start a fire with the oxygen in the room (for anesthesia) or could burn the patient before someone realizes it is no longer in the holster. Moreover, the holster often comes off of the tether and the opened tip of the pen could be exposed on the operating field. Just leaning on the drapes, for example, can then actuate the opened trigger. Further the pen can be dropped into the field and while under a retractor type instrument, continuous actuation can occur resulting in severe burns or fire.

As can be seen, there is a need for a protective cautery pen tip cover that protects the pen tip and prevents accidental actuation of the pen trigger.

SUMMARY OF THE INVENTION

Embodiments of the present invention provide an electrode pen safety system comprising a stabilization system having a track disposed along a longitudinal axis thereof and a connection member operable to secure an electrode pen thereto; a sleeve slidably received on the track, the sleeve having a first end operable to receive the electrode pen therein, and a second opposite end, operable to permit an electrode pen tip to extend therefrom; and a trigger actuation opening formed as a through hole in the sleeve, the trigger actuation opening positioned to permit a user to activate a trigger of the electrode pen when the electrode pen is secured by the connection member of the stabilization system and the sleeve is positioned in a retracted configuration with the electrode pen tip extending beyond the second opposite end of the sleeve, the sleeve preventing access to the trigger when positioned in a non-retracted position, with the sleeve surrounding the electrode pen tip.

Embodiments of the present invention further provide a sleeve for an electrode pen, comprising a first end operable to receive the electrode pen therein; a second opposite end, operable to permit an electrode pen tip to extend therefrom; a trigger actuation opening formed as a through hole in the sleeve, the trigger actuation opening positioned to permit a user to activate a trigger of the electrode pen when the electrode pen is inserted therein in a retracted configuration with the electrode pen tip extending beyond the second opposite end of the sleeve, the sleeve preventing access to the trigger when positioned in a non-retracted position, with the sleeve surrounding the electrode pen tip; and a lateral opening formed as a through hole through the sleeve, the lateral opening disposed on at least one side of the sleeve and permitting direct contact with the electrode pen when the electrode pen is disposed therein.

Embodiments of the present invention also provide an electrocautery system comprising an electrode pen; a stabilization system having a track disposed along a longitudinal axis thereof and a connection member operable to secure the electrode pen thereto; a sleeve slidably received on the track, the sleeve having a first end receiving the electrode pen therein, and a second opposite end, permitting an electrode pen tip to extend therefrom; a trigger actuation opening formed as a through hole in the sleeve, the trigger actuation opening positioned to permit a user to activate a trigger of the electrode pen when the sleeve is positioned in a retracted configuration with the electrode pen tip extending beyond the second opposite end of the sleeve, the sleeve preventing access to the trigger when positioned in a non-retracted position, with the sleeve surrounding the electrode pen tip; and a compression spring disposed within the sleeve adjacent the second opposite end, the compression spring urging the sleeve to a non-retracted position.

In one aspect of the present invention, a cautery pen tip cover comprises a cylindrical member with opened exposure laterally allowing the feel of the exposed pen operable to receive a cautery pen in a first end thereof; a tip opening disposed in a second, opposite end of the cylindrical member, the tip opening permitting a tip of the cautery pen to extend therethrough when the cautery pen tip cover is in a retracted configuration; a cover exposure opening formed in the cylindrical member, the cover exposure opening providing access to a trigger of the cautery pen when the cautery pen tip cover is in the retracted configuration, wherein the cautery pen tip cover prevents access to the trigger when the cautery pen tip cover is in a non-retracted configuration; and a resilient member operable to urge the cautery pen tip cover to the non-retracted configuration. The cylindrical member is easily retracted by a finger ring with a raised surface configured permanently into the cylindrical member allowing easy retraction in a natural closed hand position of the operator squeezed to a resistance bar stabilization system accessory configured over the body of the pen.

In another aspect of the present invention, a cautery pen tip cover comprises a cylindrical member with opened exposure laterally allowing the feel of the exposed pen operable to receive a cautery pen in a first end thereof; a tip opening disposed in a second, opposite end of the cylindrical member, the tip opening permitting a tip of the cautery pen to extend therethrough when the cautery pen tip cover is in a retracted configuration by squeezing the finger rings against the resistance bar accessory in a natural closed hand position; a cover exposure opening formed in the cylindrical member, the cover exposure opening providing access to a trigger of the cautery pen when the cautery pen tip cover is in the retracted configuration, wherein the cautery pen tip cover prevents access to the trigger when the cautery pen tip cover is in a non-retracted configuration; a compression spring operable to urge the cautery pen tip cover to the non-retracted configuration; the one or more cover notch guides formed on an inside surface of the cylindrical member identically fits into the notch guides formed in the stabilization system, which consists of the tracks, the resistance bar and the receptacle for an optional hollow tube suction system attached to the cautery pen; and at least one cover finger plate extending from the cylindrical member at the first end thereof.

In a further aspect of the present invention, a cautery system comprises a cautery pen; and a cautery pen tip cover with exposed lateral openings, the cautery pen tip cover comprises a cylindrical member operable to receive the cautery pen in a first end thereof; a tip opening disposed in a second, opposite end of the cylindrical member, the tip opening permitting a tip of the cautery pen to extend therethrough when the cautery pen tip cover is in a retracted configuration; a cover exposure opening formed in the cylindrical member, the cover exposure opening providing access to a trigger of the cautery pen when the cautery pen tip cover is in the retracted configuration, wherein the cautery pen tip cover prevents access to the trigger when the cautery pen tip cover is in a non-retracted configuration; and a resilient member operable to urge the cautery pen tip cover to the non-retracted configuration.

In a further aspect of the present invention, the cautery system is simplified and comprises a stabilization system including a resistance bar, a track with an optional suction-tubing reservoir that is attached in one piece by a wrapped configuration on one end and spot welding on the opposite end to allow flawless retraction of the cautery pen tip/trigger cover; a two part system which does not alter the original pen but is a simple accessory system with a resilient member which urges the cautery cover in the non-retracted position.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figure 1:
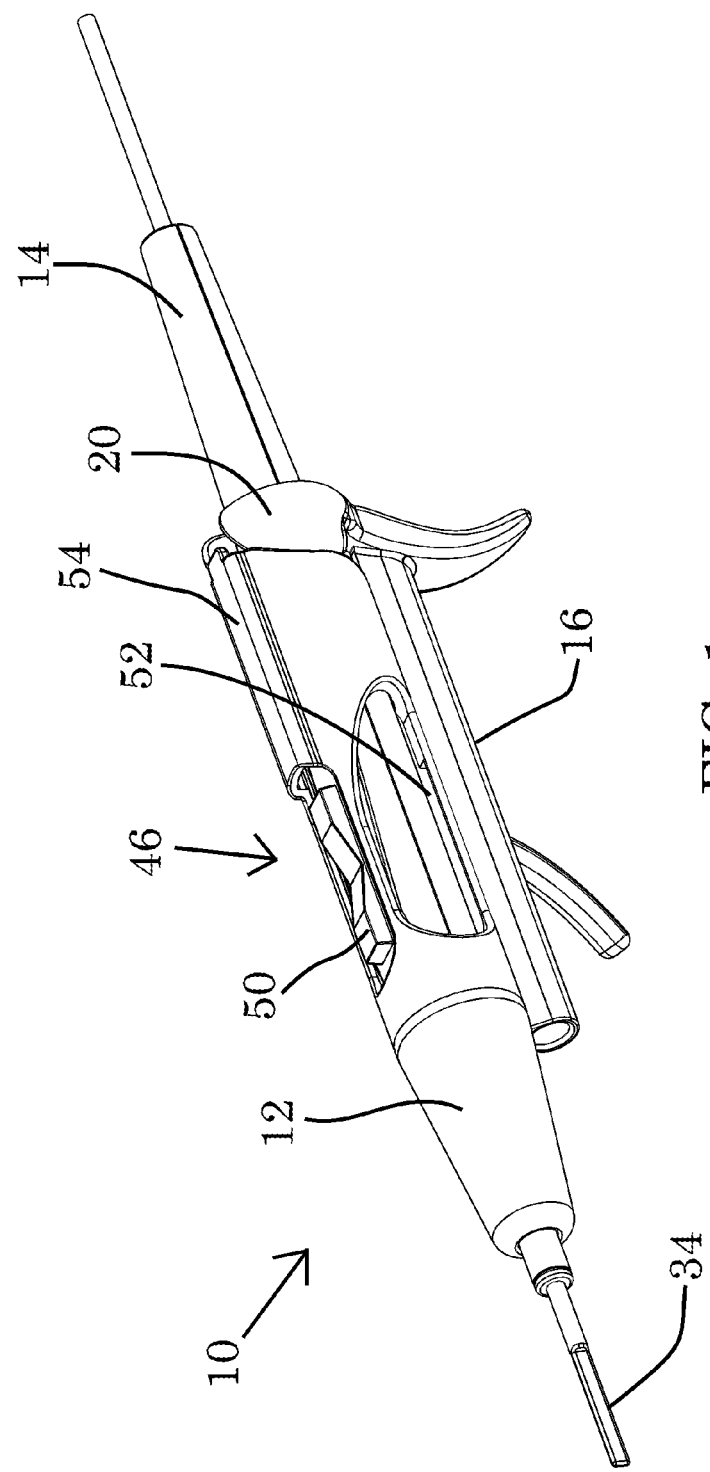
FIG. 1 illustrates a perspective view of a cautery pen accessory cover mounted on a stabilization bar system with the pen disposed therein in an actuated position, according to an exemplary embodiment of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary, a variety of optional components are described to illustrate the wide variety of possible embodiments of the present invention.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide a cautery pen tip accessory cover that comprises a cylindrical member that can receive a cautery pen in a first end and the tip of the cautery pen can extend from a second opposite end when the cover is in a retracted configuration. The cylindrical member has an opened lateral exposure that allows the feel of the cautery pen therethrough. A cover exposure opening, also referred to as a trigger actuation opening, in the cylindrical member to provide access to a trigger of the cautery pen when the cautery pen tip cover is in the retracted configuration. A resilient member urges the cautery pen tip cover to the non-retracted configuration where access to the cautery pen trigger is prevented. The cylindrical member is easily retracted by a finger ring configured permanently into the cylindrical member, allowing easy retraction of the cover by the operator squeezing the cover to a resistance bar stabilization system accessory configured over the cautery pen.

The simplicity of the cautery system is that the cautery pen does not have to be altered, other than the addition of injection molded plastic attachments, to achieve the final product. The compression spring specifications can be designed to provide appropriate retraction of the cautery pen tip into the cover when the pen is not maintained in the retracted configuration. There is simply no other mechanism that assures coverage of the electrode tip other than a permanently attached sleeve that forces compliance by the operator by removing the option of utilizing a holster that is clumsy and remote from the device. This sleeve requires retraction to actuate the device and remains covered in the non-use state. This reduces accidental actuation, burns and operating room fires by covering the source for ignition.

Referring now to FIGS. 1 through 5 and 10, a cautery pen safety system 10, also referred to as safety system 10 or simply, system 10, can include an accessory sleeve 12 that can cover the tip of an electrode pen 14, also referred to as a cautery pen 14. The sleeve 12 can be easily added to a conventional electrode pen. The sleeve 12 can move along a track 18 of a stabilization system 16 while the electrode pen 14 is fixed to a pen wrap portion 20 of the stabilization system 16.

Figure 2:
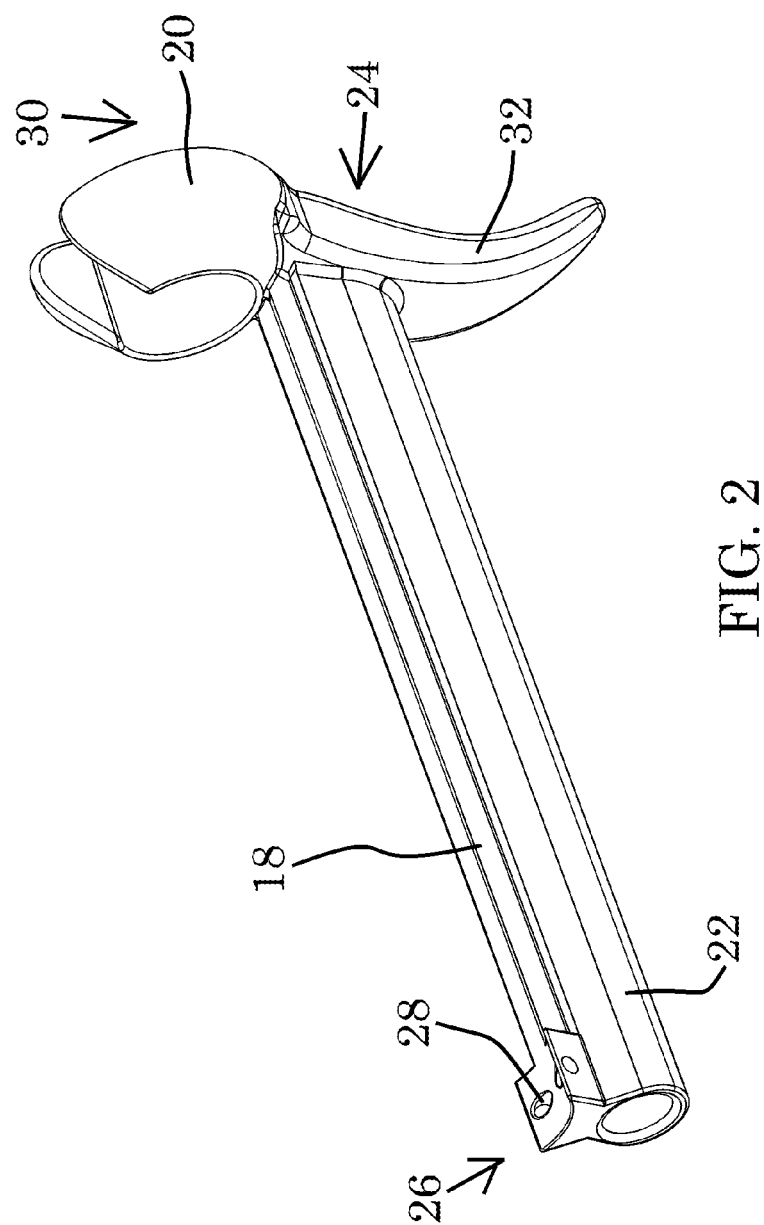
FIG. 2 illustrates a perspective view of the stabilization bar system of FIG. 1, separate from the pen, showing a track, with guide notches and an optional tubing track, for receiving the cautery pen accessory cover according to an exemplary embodiment of the present invention.

Referring specifically to FIG. 2, the stabilization system 16 can include the track 18 extending longitudinally along a length of the stabilization system 16. A suction tube 22 may be disposed below or adjacent the track 18. In use, suction may be applied to a suction tube distal end 24 to create, for example, a built-in smoke evacuator for use during cauterization.

Figure 11:
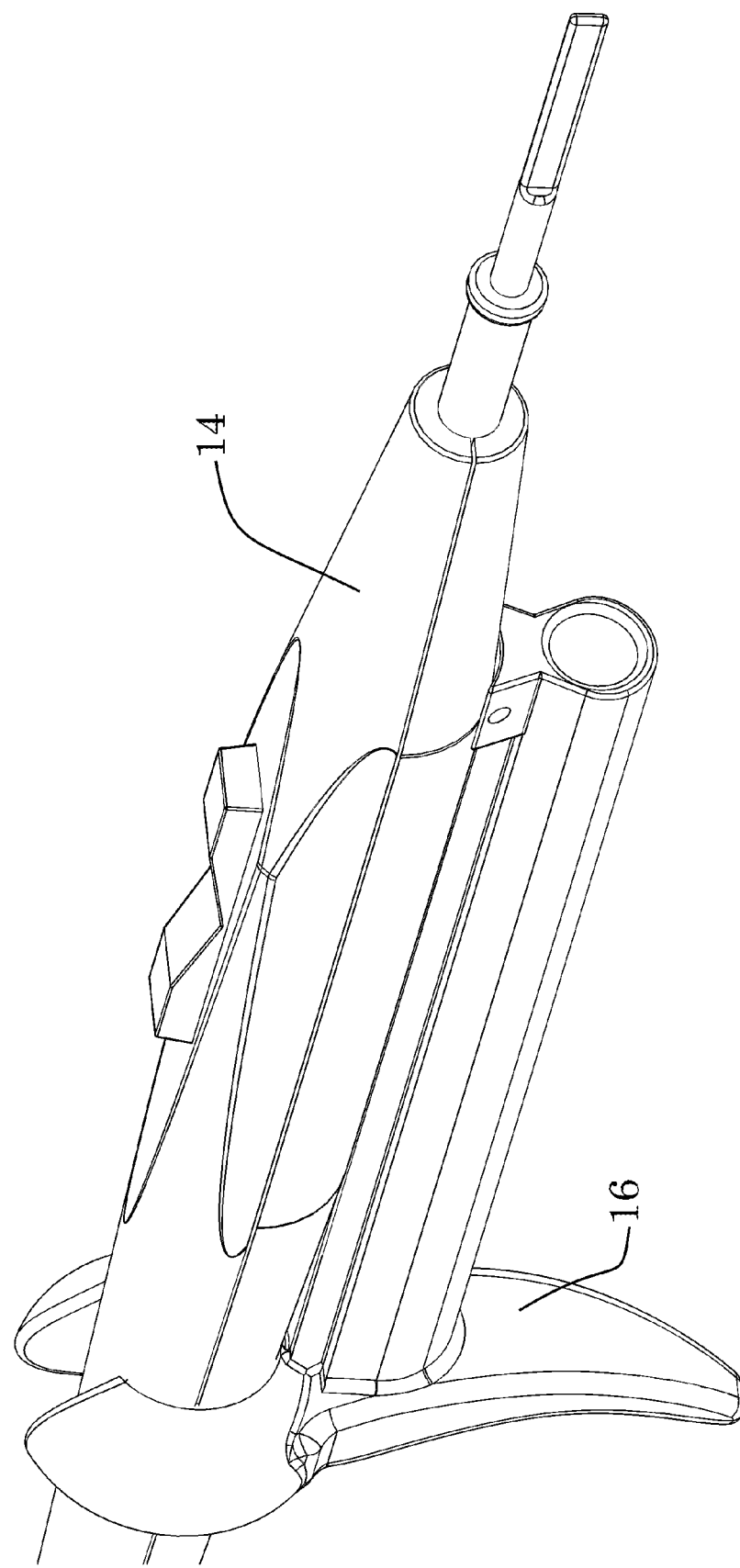
FIG. 11 illustrates a perspective view of a cautery pen disposed in the stabilization bar system without the accessory cover installed thereupon.

A proximate end 26 of the stabilization system 16 can include one or more spot welds 28, or similar protrusions can allow direct attachment of the electrode pen 14 to the stabilization system 16. A distal end 30 of the stabilization system 16 can include the pen wrap portion 20 which can be configured to secure the electrode pen 14 therein, as shown in FIGS. 1 and 11. The pen wrap portion 20 may be a friction fitting member, or may include one or more securement mechanisms (not shown) for fixing the electrode pen 14 thereto. The securement mechanisms may include set screws, tightening members, or the like. In some embodiments, the electrode pen 14 may be made integrally with the stabilization system 16. In this embodiment, the pen wrap portion 20 may not be necessary since the pen 14 is already affixed to the integral stabilization system.

A resistance bar 32 may extend, at or near the distal end 30, away from the pen wrap portion 20 to provide a fixed extension effectively attached to the electrode pen 14 that assists in the use and retraction of a tip 34 of the electrode pen 14 from the sleeve 12.

Figure 3:
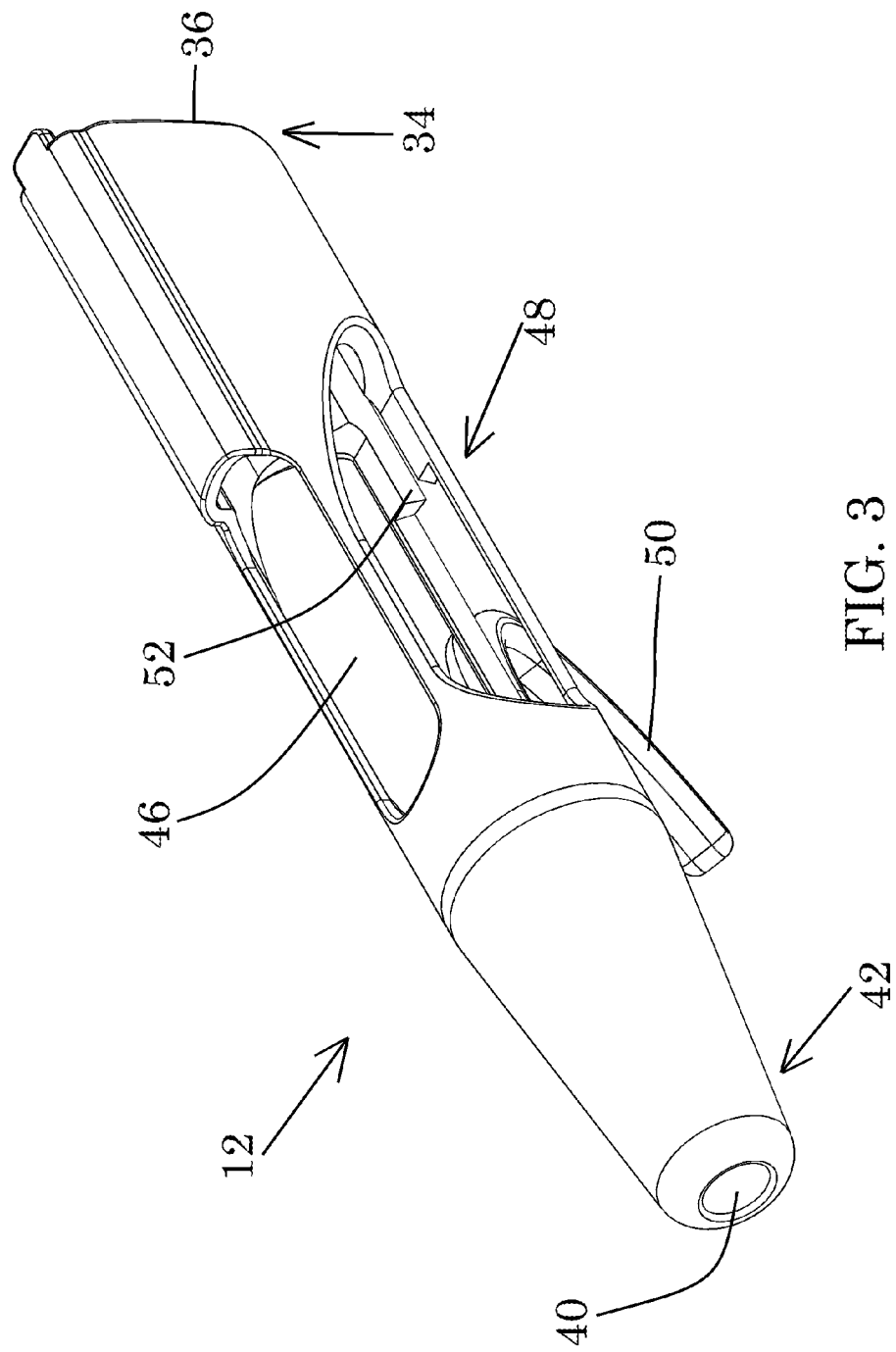
FIG. 3 illustrates a side view of the cautery pen accessory cover, partially cut away to show a spring therewithin, according to an exemplary embodiment of the present invention.
Figure 4:
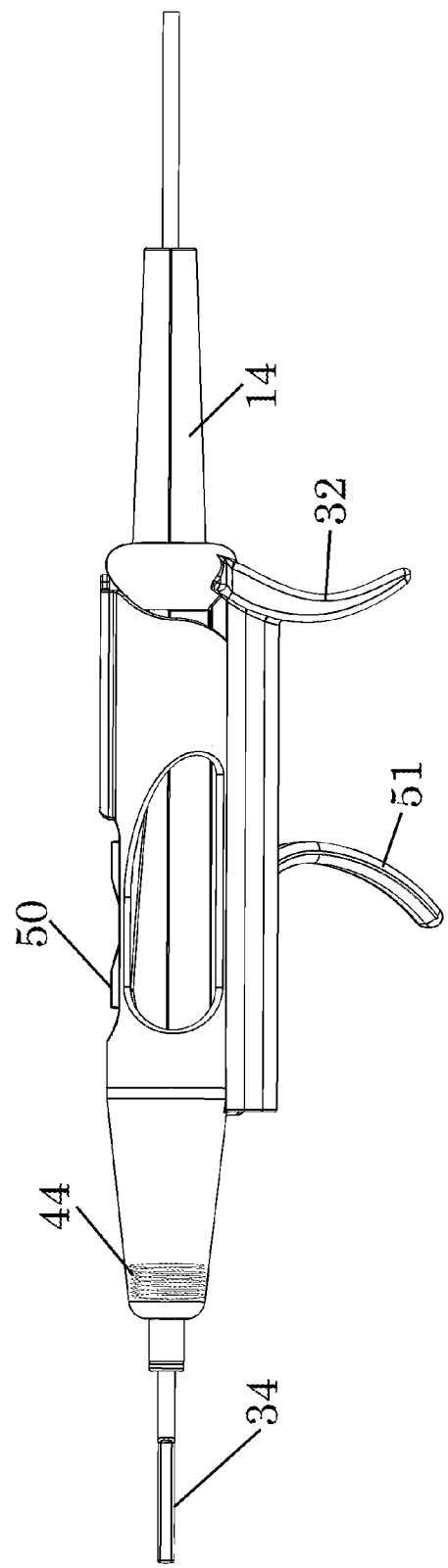
FIG. 4 illustrates a left side view of the cautery pen accessory cover/stabilization bar system of FIG. 1.
Figure 5:
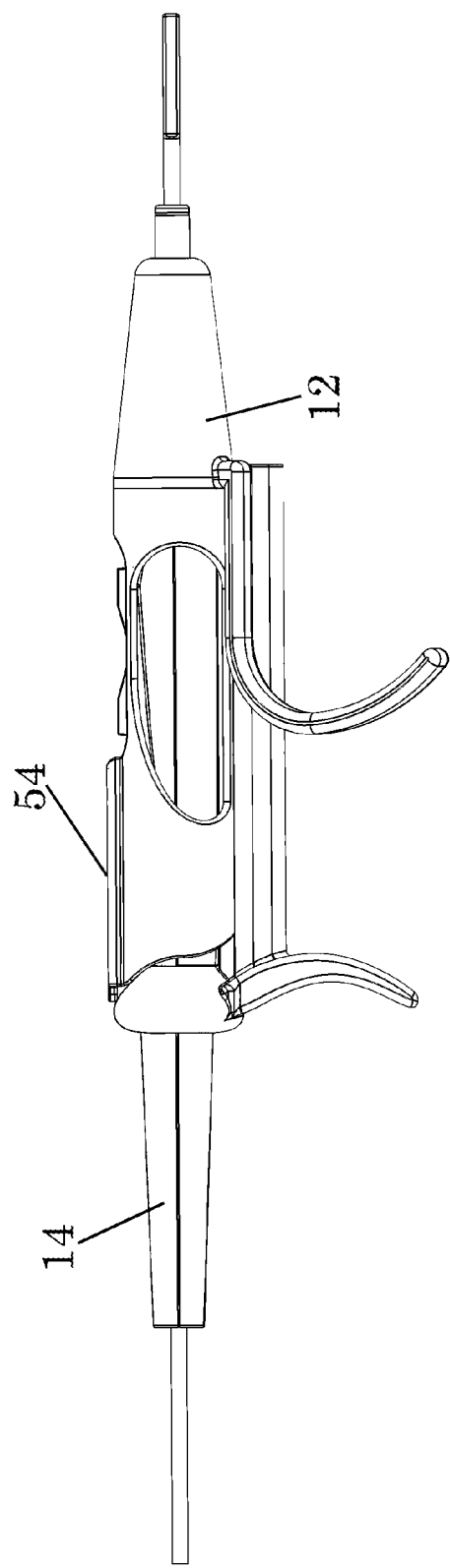
FIG. 5 illustrates a right side view of the cautery pen accessory cover/stabilization bar system of FIG. 1.

Referring now to FIGS. 3 through 5, the sleeve 12 can include a first opening 36 at a sleeve distal end 38 into which the electrode pen 14 can fit. A tip opening 40 can be formed in a sleeve proximate end 42 of the sleeve 12. A compression spring 44 may be disposed inside the sleeve 12, at the sleeve proximate end 42. The compression spring 44 may be sized too large to extend out of the sleeve proximate end 42 but may be small enough to press against an electrode pen body tip end 46, from which the electrode tip 34 extends. The effect is that the sleeve 12 may be disposed over the electrode pen 14 and, as the sleeve 12 is retracted to expose the electrode pen tip 34 out from the tip opening 40 of the sleeve 12, the compression spring 44 urges the sleeve 12 to move in an opposite direction to cover the electrode pen tip 34. The compression spring 44 may be fixed inside of the sleeve 44 or may simply be removably disposed therein.

The sleeve 12 can include a trigger actuation opening 46 formed as a hole through a portion of the sleeve 12. The trigger actuation opening 46 is positioned such that when the sleeve 12 is in a non-retracted position (see FIG. 6), the sleeve 12 prevents access to a trigger 50 of the electrode pen 14. However, when the sleeve 12 is moved, against the resiliency of the compression spring 44, into the retracted configuration (as shown in FIGS. 1 and 4, for example), the electrode pen tip 34 extends from the tip opening 40 and the trigger 50 is accessible through the trigger actuation opening 46. Should the unit be dropped or set aside, the resiliency of the compression spring 44 can cause the sleeve to slide along the track 18 (see FIG. 2) of the stabilization system 16 into the non-retracted configuration, where the electrode pen tip 34 is protected inside the sleeve 12 and the trigger 50 is non-accessible, covered by the sleeve 12.

The sleeve 12 can include a lateral opening 48 along at least a portion of the side of the sleeve 12. The lateral opening 48 can be formed on one or both sides of the sleeve 12 and allows the user direct contact with the electrode pen 14 disposed in the sleeve 12. Typically, the lateral opening 48 is disposed between the trigger actuation opening 46 and the bottom of the sleeve 12, where the sleeve 12 rides along the track 18 of the stabilization system 16. In some embodiments, the lateral opening 48 may be disposed to be longer or shorter than a length of the trigger actuation opening 46.

Figure 7:
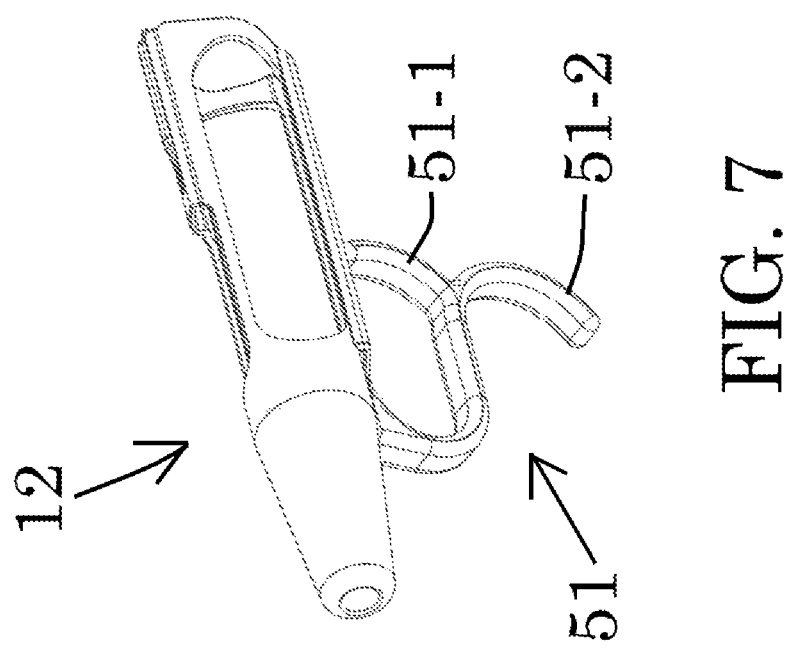
FIG. 7 illustrates a perspective view of a cautery pen accessory cover according to an alternate embodiment of the present invention.
Figure 8:
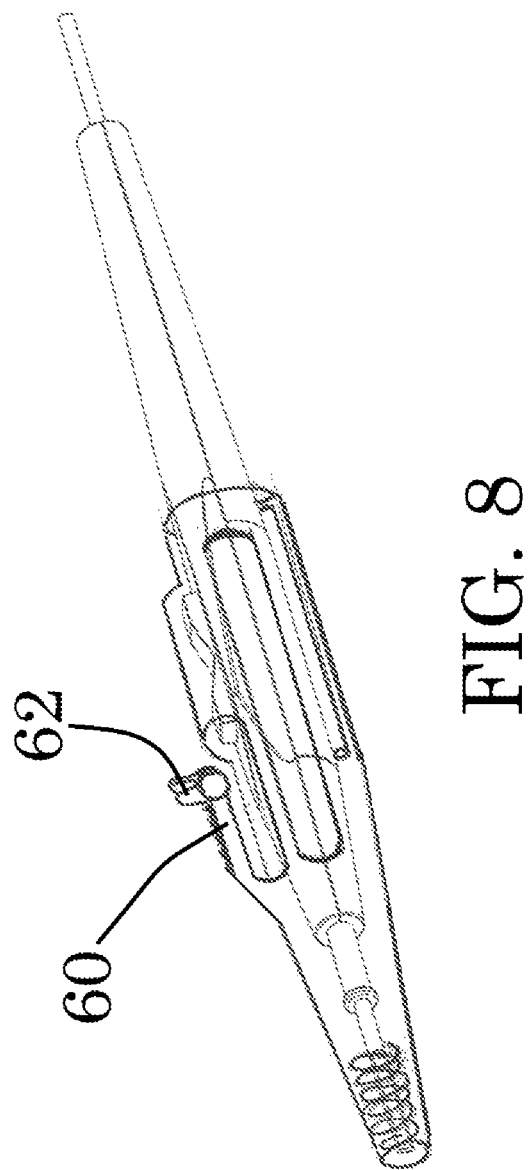
FIG. 8 illustrates a perspective view of a cautery pen accessory cover according to an alternate embodiment of the present invention.

The sleeve 12 can include a finger ring 51 affixed to a portion of the sleeve 12 and extending downward (toward the stabilization system 16 when the system 10 is assembled, as shown in FIG. 4, for example). The finger ring 51 may be formed as a curved bar, as shown in FIG. 4, or may have other shapes, such as a ring shape as shown in FIG. 7, or may be excluded, as shown in FIG. 8, for example. The finger ring 51 may be used to assist the user in retracting the sleeve 12 by, for example, allowing the user to squeeze the finger ring 51 toward the resistance bar 32 to achieve the retracted configuration of FIG. 4.

When not in use, the operator releases the sleeve 12 and the compression spring 44 recoils, covering the electrode pen tip 34 and is stopped by a graduated ring or trigger lever (not shown), or other like mechanism, that prevents the base of the sleeve 12 from propelling completely off of the electrode pen 14 and stops at the point that the electrode pen tip 34 is completely covered.

Figure 6:
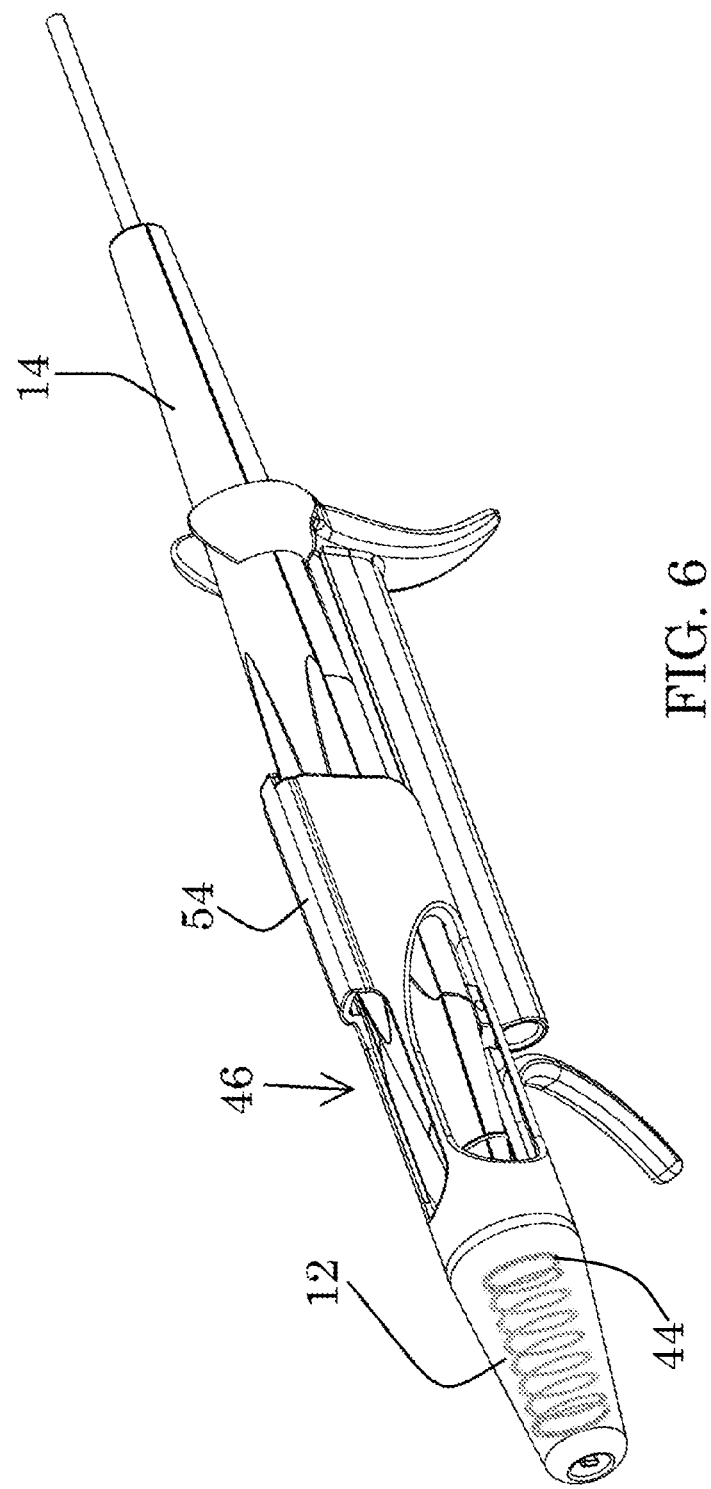
FIG. 6 illustrates a perspective view of the cautery pen accessory cover/stabilization bar system of FIG. 1, showing the cautery pen in a non-retracted, protected position.

Referring now to FIGS. 1 and 6, one can see how the sleeve 12 can be moved from the non-retracted position as shown in FIG. 6, where the trigger actuation opening 46 does not allow activation of the trigger 50 (not shown, but covered by a portion 54 of the sleeve 12), to the retracted position as shown in FIG. 1, where the electrode pen tip 34 extends from the sleeve 12 and the trigger actuation opening 46 allows a user to directly contact the trigger 50 of the electrode pen 14. It should be noted that, in some embodiments, the portion 54 of the sleeve 12 that covers the trigger 50 of the electrode pen 14 may be raised, as shown in FIG. 6, thereby allowing the electrode pen 14 to move linearly through the sleeve 12.

The sleeve 12 may include a channel 52 or a set of grooves or protrusions formed along the bottom thereof to receive the track 18 of the stabilization system 16. This configuration allows the sleeve 12 to slide along the track 18 and permits the movement between the retracted (use) and non-retracted (stored) positions.

Referring to FIG. 7, in some embodiments, the sleeve 12 may be formed from a varied design. For example, the finger ring 51 may include a ring portion 51-1 and an extending portion 51-2. Of course, other configurations are contemplated within the scope of the present invention.

Figure 9:
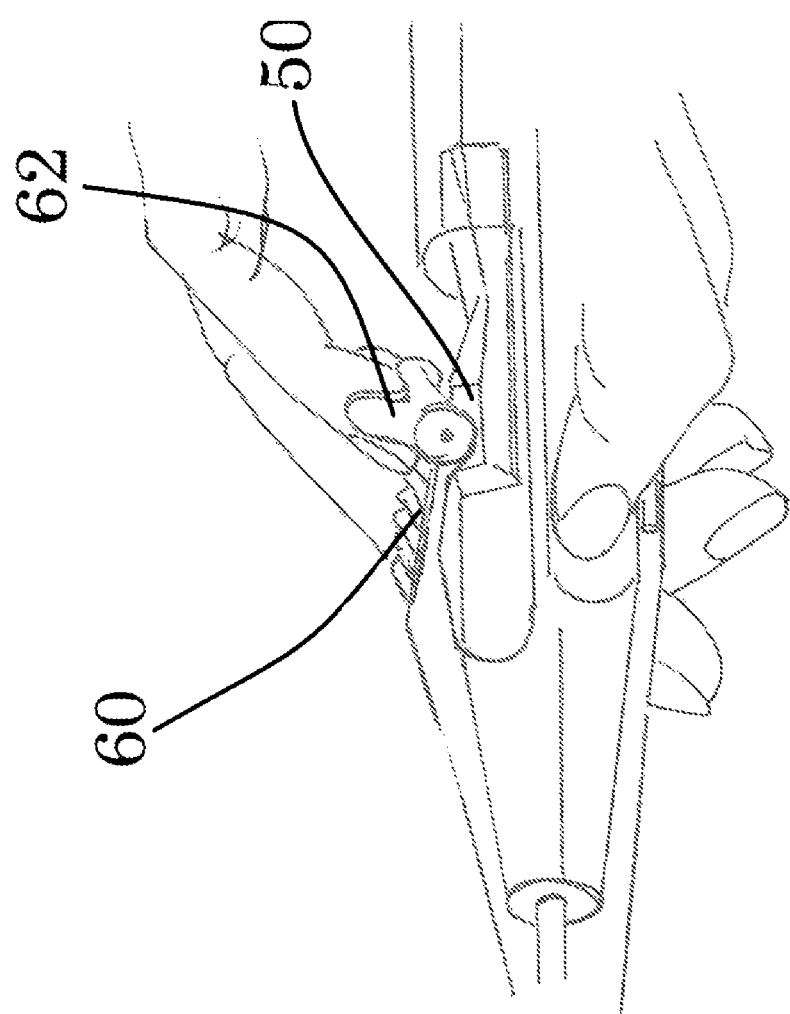
FIG. 9 illustrates a detailed perspective view showing use of the cautery pen accessory cover of FIG. 8.
Figure 10:
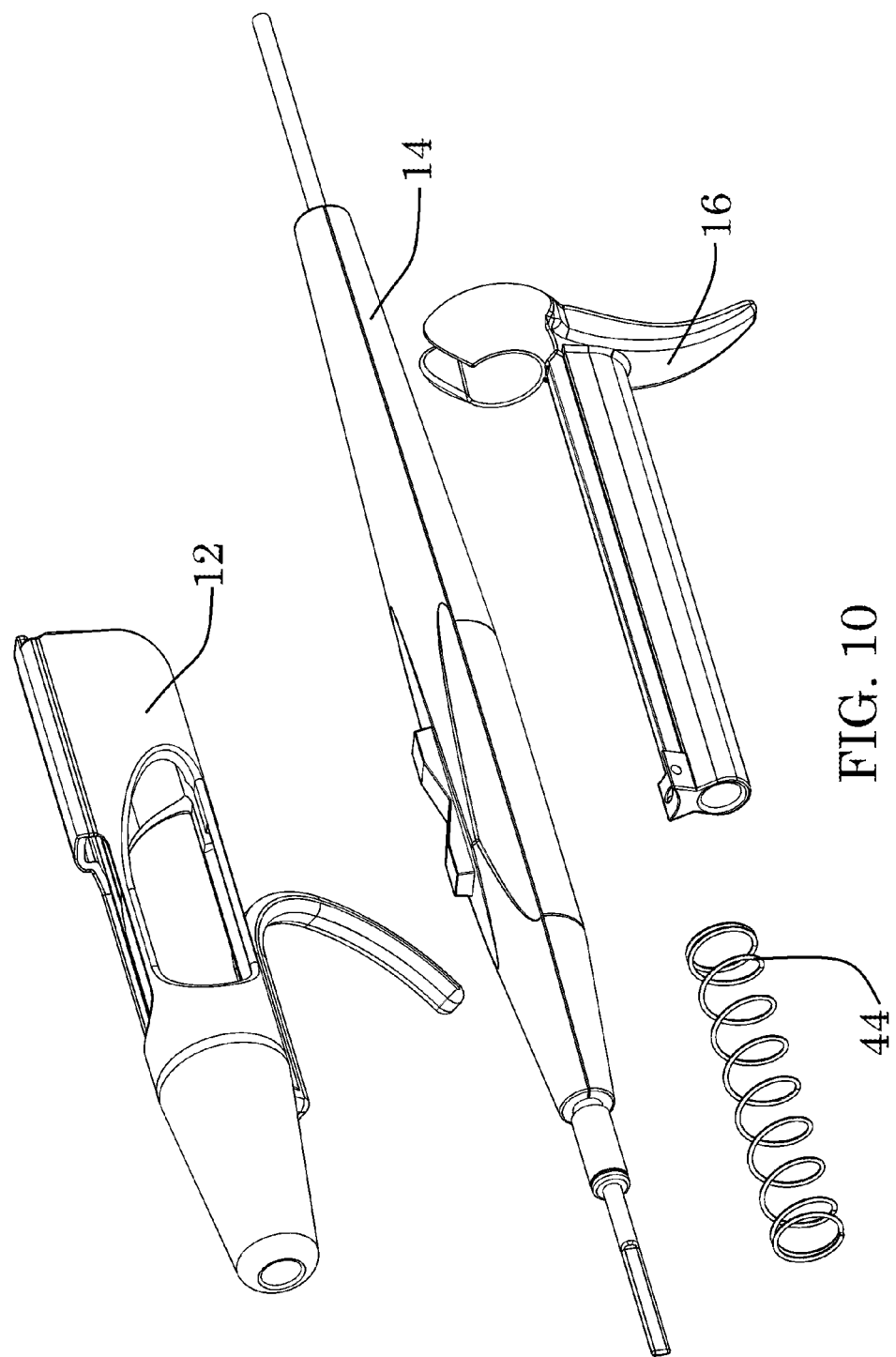
FIG. 10 illustrates an exploded perspective view of the cautery pen safety system of FIG. 1.

Referring to FIGS. 8 and 9, in some embodiments, the sleeve 12 can include a flexible actuation member 60 that may extend over the trigger actuation opening 46 as shown in FIG. 9. The actuation member 60 may include a textured outer surface for receiving a user's finger. When the system is in the retracted configuration, the trigger 50 may be disposed below the actuation member 60, which the user may flexibly depress against the trigger 50 to actuate the electrode pen 14. In some embodiments, finger stabilization side members 62 may be disposed on opposite sides of the flexible actuation member 60

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. An electrode pen safety system comprising:
   a stabilization system having a track disposed along a longitudinal axis thereof and a connection member operable to secure an electrode pen thereto;
   a sleeve slidably received on the track, the sleeve having a first end operable to receive the electrode pen therein, and a second opposite end, operable to permit an electrode pen tip to extend therefrom; and
   a trigger actuation opening formed as a through hole in the sleeve, the trigger actuation opening positioned to permit a user to directly contact and activate a trigger of the electrode pen when the electrode pen is secured by the connection member of the stabilization system and the sleeve is positioned in a retracted configuration with the electrode pen tip extending beyond the second opposite end of the sleeve, the sleeve preventing access to the trigger when positioned in a non-retracted position, with the sleeve surrounding the electrode pen tip.

2. The electrode pen safety system of claim 1, further comprising a lateral opening formed as a through hole through the sleeve, the lateral opening disposed on at least one side of the sleeve and permitting direct contact with the electrode pen when the electrode pen is secured by the connection member of the stabilization system.

3. The electrode pen safety system of claim 1, further comprising a resistance bar extending from the stabilization system, the resistance bar affixed at a distal end of the track.

4. The electrode pen safety system of claim 1, further comprising a spot weld on a proximate end of the track, the spot weld operable to affix the electrode pen thereto.

5. The electrode pen safety system of claim 1, further comprising a finger ring extending from the sleeve.

6. The electrode pen safety system of claim 1, further comprising a compression spring disposed within the sleeve adjacent the second opposite end, the compression spring urging the sleeve to a non-retracted position when the electrode pen is secured by the connection member of the stabilization system.

7. The electrode pen safety system of claim 1, further comprising a tube disposed adjacent the track.

8. The electrode pen safety system of claim 1, further comprising a raised portion of the sleeve, the raised portion of the sleeve permitting the trigger of the electrode pen to fit thereunder when the sleeve is placed onto the electrode pen, the raised portion preventing access to the trigger when the sleeve is in the non-retracted configuration.

9. The electrode pen safety system of claim 1, wherein the connection member wraps about at least a portion of the electrode pen when the electrode pen is secured therein.

10. The electrode pen safety system of claim 1, wherein the stabilization system is integrally formed into the electrode pen.

11. A sleeve for an electrode pen, comprising:
a first end operable to receive the electrode pen therein;
a second opposite end, operable to permit an electrode pen tip to extend therefrom;
a trigger actuation opening formed as a through hole in the sleeve, the trigger actuation opening positioned to permit a user to directly contact and activate a trigger of the electrode pen when the electrode pen is inserted therein in a retracted configuration with the electrode pen tip extending beyond the second opposite end of the sleeve, the sleeve preventing access to the trigger when positioned in a non-retracted position, with the sleeve surrounding the electrode pen tip; and
a lateral opening formed as a through hole through the sleeve, the lateral opening disposed on at least one side of the sleeve and permitting direct contact with the electrode pen when the electrode pen is disposed therein.

12. The sleeve of claim 11, further comprising a finger ring extending from the sleeve.

13. The sleeve of claim 11, further comprising a compression spring disposed within the sleeve adjacent the second opposite end, the compression spring urging the sleeve to a non-retracted position when the electrode pen is secured by the connection member of the stabilization system.

14. The sleeve of claim 11, further comprising a raised portion permitting the trigger of the electrode pen to fit thereunder when the sleeve is placed onto the electrode pen, the raised portion preventing access to the trigger when the sleeve is in the non-retracted configuration.

15. An electrocautery system comprising:
an electrode pen;
a stabilization system having a track disposed along a longitudinal axis thereof and a connection member operable to secure the electrode pen thereto;
a sleeve slidably received on the track, the sleeve having a first end removably receiving the electrode pen therein, and a second opposite end, permitting an electrode pen tip to extend therefrom;
a trigger actuation opening formed as a through hole in the sleeve, the trigger actuation opening positioned to permit a user to directly contact and activate a trigger of the electrode pen when the sleeve is positioned in a retracted configuration with the electrode pen tip extending beyond the second opposite end of the sleeve, the sleeve preventing access to the trigger when positioned in a non-retracted position, with the sleeve surrounding the electrode pen tip; and
a compression spring disposed within the sleeve adjacent the second opposite end, the compression spring urging the sleeve to a non-retracted position.

16. The electrocautery system of claim 15, further comprising a lateral opening formed as a through hole through the sleeve, the lateral opening disposed on at least one side of the sleeve and permitting direct contact with the electrode pen.

17. The electrocautery system of claim 15, further comprising:
a resistance bar extending from the stabilization system, the resistance bar affixed at a distal end of the track; and
a finger ring extending from the sleeve, wherein squeezing the finger ring toward the resistance bar causes the sleeve to slide along the track and move the sleeve into the retracted configuration.

18. The electrocautery system of claim 15, further comprising a tube disposed adjacent the track.

19. The electrocautery system of claim 15, wherein the connection member wraps about at least a portion of the electrode pen when the electrode pen is secured therein.

20. The electrocautery system of claim 15, wherein the stabilization system is integrally formed into the electrode pen.

* * * * *